(12) United States Patent
Doi et al.

(10) Patent No.: US 11,420,043 B2
(45) Date of Patent: Aug. 23, 2022

(54) LOW-FREQUENCY TREATMENT DEVICE, BODY FOR LOW-FREQUENCY TREATMENT DEVICE, AND COMBINATION OF PAD AND HOLDER FOR LOW-FREQUENCY TREATMENT DEVICE

(71) Applicant: OMRON HEALTHCARE CO., LTD., Muko (JP)

(72) Inventors: Yoshiki Doi, Kyoto (JP); Shinji Nakazawa, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 281 days.

(21) Appl. No.: 16/554,350

(22) Filed: Aug. 28, 2019

(65) Prior Publication Data

US 2019/0381308 A1 Dec. 19, 2019

Related U.S. Application Data

(63) Continuation of application No. PCT/JP2018/006998, filed on Feb. 26, 2018.

(30) Foreign Application Priority Data

Mar. 2, 2017 (JP) .............................. JP2017-039637

(51) Int. Cl.
*A61N 1/04* (2006.01)
*H05K 1/11* (2006.01)
*A61N 1/36* (2006.01)

(52) U.S. Cl.
CPC .......... *A61N 1/0492* (2013.01); *A61N 1/0488* (2013.01); *A61N 1/36014* (2013.01); *H05K 1/112* (2013.01)

(58) Field of Classification Search
CPC ... A61N 1/0452; A61N 1/0456; A61N 1/0492
See application file for complete search history.

(56) References Cited

U.S. PATENT DOCUMENTS 10,702,691 B2 * 7/2020 Doi ...................... A61N 1/0452
2002/0060579 A1 5/2002 Haseyama et al.
(Continued)

FOREIGN PATENT DOCUMENTS

DE 112016004017 T5 5/2018
JP H01-221174 A 9/1989
(Continued)

OTHER PUBLICATIONS

Aug. 4, 2020 Office Action issued in Japanese Patent Application No. 2017-039637.
(Continued)

*Primary Examiner* — Alyssa M Alter
(74) *Attorney, Agent, or Firm* — Oliff PLC

(57) ABSTRACT

A low-frequency treatment device includes a pad including a through hole and a pad side electrode on a rear surface, a holder disposed on the rear surface side of the pad so as to oppose the pad side electrode, a body including a body side electrode and detachably attached to the holder, and a wiring member configured to electrically connect the body side electrode and the pad side electrode. The wiring member includes a first end portion connected to the body side electrode, a second end portion connected to the pad side electrode, and a conductive portion, disposed such that a portion of the conductive portion extends through a through hole, for conducting electricity between the first end portion and the second end portion.

6 Claims, 11 Drawing Sheets

(56) References Cited

U.S. PATENT DOCUMENTS

2011/0224754 A1  9/2011 Wei
2018/0177998 A1  6/2018 Doi et al.

FOREIGN PATENT DOCUMENTS

| JP | H06-339531 A | 12/1994 |
| JP | H10-323401 A | 12/1998 |
| JP | H11-162270 A | 6/1999 |
| JP | 2009-005993 A | 1/2009 |
| JP | 3158303 U | 3/2010 |
| JP | 2015-047382 A | 3/2015 |
| WO | 2017/038467 A1 | 3/2017 |

OTHER PUBLICATIONS

May 1, 2018 International Search Report issued in International Patent Application No. PCT/JP2018/006998.
Jun. 18, 2021 Office Action issued in German Patent Application No. 11 2018 001 084.8.

* cited by examiner

LOW-FREQUENCY TREATMENT DEVICE, BODY FOR LOW-FREQUENCY TREATMENT DEVICE, AND COMBINATION OF PAD AND HOLDER FOR LOW-FREQUENCY TREATMENT DEVICE

TECHNICAL FIELD

The present invention relates to a low-frequency treatment device.

BACKGROUND ART

In a low-frequency treatment device described in Patent Document 1 (JP H06-339531 A), a treatment device body is configured to include an upper half portion (body) and a lower half portion (holder), and a pad is disposed between the upper half portion and the lower half portion. The pad includes a front surface and a rear surface, and the top half portion of the body is disposed on the front surface side of the pad, and the lower half portion of the body is disposed on the rear surface side of the pad. The pad side electrode is provided on the rear surface side of the pad.

A pair of connection terminals are provided on the lower surface of the upper half portion of the body, and a pair of connection terminals are provided on the upper surface of the lower half portion of the body. The upper half portion can be assembled together with the lower half portion by fitting a projection provided on the lower half portion into a recess portion provided in the upper half portion. By disposing the pad between the upper half portion and the lower half portion and assembling the upper half portion together with the lower half portion, conductivity is established between the pair of connection terminals provided on the upper half portion and the pair of connection terminals provided on the lower half portion, and conductivity is established between the pair of connection terminals provided on the lower half portion and a pad side electrode provided on the rear surface side of the pad.

CITATION LIST

Patent Literature

Patent Document 1: JP H06-339531 A

SUMMARY OF INVENTION

Technical Problem

In the low-frequency treatment device disclosed in Patent Document 1 (JP H06-339531 A), conductivity is established from the pad side electrode provided on the rear surface side of the pad to the pair of connection terminals (body side electrodes) provided on the upper half portion via the pair of connection terminals provided on the lower half portion. When the pad is viewed in a plan view, the pair of connection terminals provided on the upper half portion and the pair of connection terminals provided on the lower half portion are connected to each other at a position outward from a peripheral edge of the pad (see FIG. 4 of Patent Document 1). This configuration makes it difficult to reduce the size of the upper half portion (the body) and the lower half portion (the holder), and thus makes it difficult to reduce the overall size of the low-frequency treatment device.

An object of the present invention is to provide a low-frequency treatment device, a body for a low-frequency treatment device, and a combination of a pad and a holder for a low-frequency treatment device that are configured to be capable of reducing the sizes thereof.

Solution to Problem

An embodiment is a low-frequency treatment device, including, a pad including a front surface, a rear surface, a through hole that extends from the front surface to the rear surface, and a pad side electrode formed on the rear surface, a holder including a plate-like portion, the holder being disposed on the rear surface side of the pad such that the plate-like portion opposes the pad side electrode, a body including an opposite surface and a body side electrode provided on the opposite surface side, the body being disposed such that the opposite surface opposes the front surface of the pad and the body being detachably attached to the holder so as to sandwich the pad between the opposite surface and the holder, and a wiring member configured to electrically connect the body side electrode and the pad side electrode, wherein the wiring member includes a first end portion connected to the body side electrode, a second end portion connected to the pad side electrode, and a conductive portion, disposed such that a portion of the conductive portion extends through the through hole, for conducting electricity between the first end portion and the second end portion.

In the low-frequency treatment device described above, preferably, the holder includes a projection portion provided to project from the plate-like portion, in a state where the holder is disposed on the rear surface side of the pad, the projection portion is disposed extending through the through hole of the pad, and the portion of the conductive portion of the wiring member disposed to extend through the through hole is held by the projection portion.

In the low-frequency treatment device described above, preferably, an insertion opening is formed in the opposite surface of the body, the body side electrode is provided inside the insertion opening, and in a state where the body is attached to the holder, the projection portion is inserted into the insertion opening and the first end portion and the body side electrode are brought into contact with one another.

In the low-frequency treatment device described above, preferably, the conductive portion of the wiring member includes a first elastic portion located on the first end portion side, and the first end portion is brought into contact with the body side electrode by biasing force of the first elastic portion.

In the low-frequency treatment device described above, preferably, the conductive portion of the wiring member includes a second elastic portion located on the second end portion side, and the second end portion is brought into contact with the pad side electrode by biasing force of the second elastic portion.

In the low-frequency treatment device described above, preferably, a step region is provided to be recessed in the plate-like portion of the holder, and the conductive portion of the wiring member includes a portion disposed inside the step region.

In the low-frequency treatment device described above, preferably, the rear surface of the pad and the plate-like portion of the holder are joined together via an adhesive portion.

An embodiment is a body, included in a low-frequency treatment device, for the low-frequency treatment device including a pad including a front surface, a rear surface, a through hole that extends from the front surface to the rear surface, and a pad side electrode formed on the rear surface, and a holder including a plate-like portion, the holder being disposed on the rear surface side of the pad such that the plate-like portion opposes the pad side electrode, the body including an opposite surface and a body side electrode provided on the opposite surface side, the body being disposed such that the opposite surface opposes the front surface of the pad and the body being detachably attached to the holder so as to sandwich the pad between the opposite surface and the holder. The low-frequency treatment device further includes a wiring member configured to electrically connect the body side electrode and the pad side electrode, the wiring member includes a first end portion connected to the body side electrode, a second end portion connected to the pad side electrode, and a conductive portion, disposed such that a portion of the conductive portion extends through the through hole, for conducting electricity between the first end portion and the second end portion.

Another embodiment is a combination of a pad and a holder for a low-frequency treatment device, wherein the pad includes a front surface, a rear surface, a through hole that extends from the front surface to the rear surface, and a pad side electrode formed on the rear surface, the holder includes a plate-like portion, the holder being disposed on the rear surface side of the pad such that the plate-like portion opposes the pad side electrode, the low-frequency treatment device includes a body including an opposite surface and a body side electrode provided on the opposite surface side, the body being disposed such that the opposite surface opposes the front surface of the pad and the body being detachably attached to the holder so as to sandwich the pad between the opposite surface and the holder, and a wiring member configured to electrically connect the body side electrode and the pad side electrode, the wiring member including a first end portion connected to the body side electrode, a second end portion connected to the pad side electrode, and a conductive portion, disposed such that a portion of the conductive portion extends through the through hole, for conducting electricity between the first end portion and the second end portion.

Advantageous Effects of Invention

According to the configurations described above, a low-frequency treatment device, a body for a low-frequency treatment device, and a combination of a pad and a holder for a low-frequency treatment device can be obtained that are configured to be capable of reducing the sizes thereof.

DESCRIPTION OF EMBODIMENTS

Figure 1:
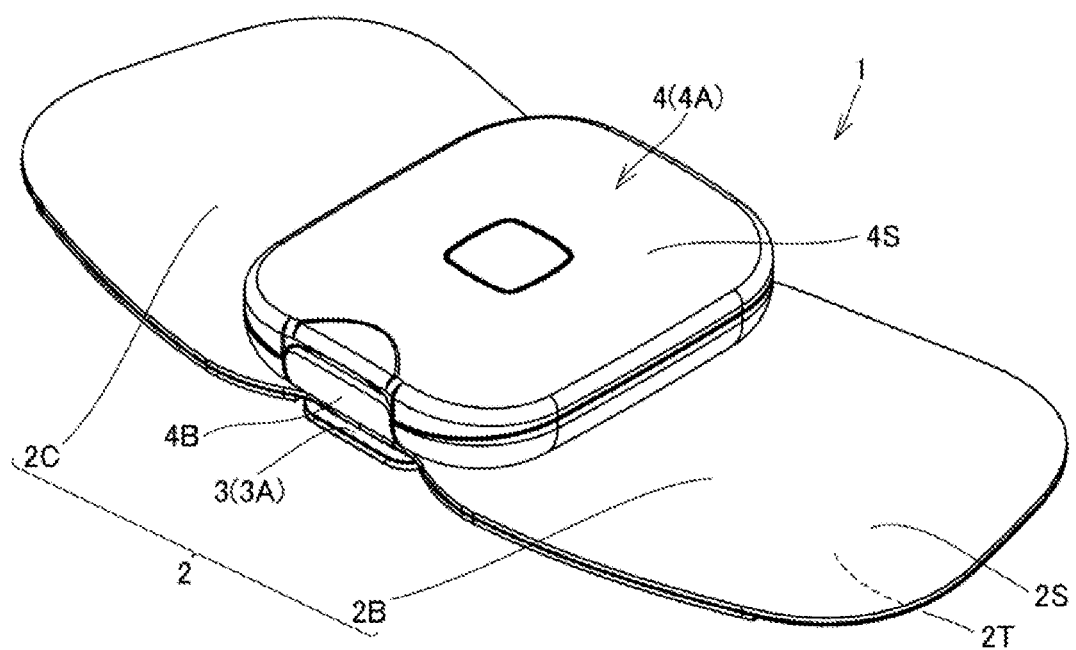
FIG. 1 is a perspective view illustrating a low-frequency treatment device 1 according to an embodiment.

A low frequency treatment 1 according to an embodiment will be described below with reference to the drawings. The same reference numerals are assigned to same or equivalent parts, and redundant descriptions may not be repeated.

Figure 2:
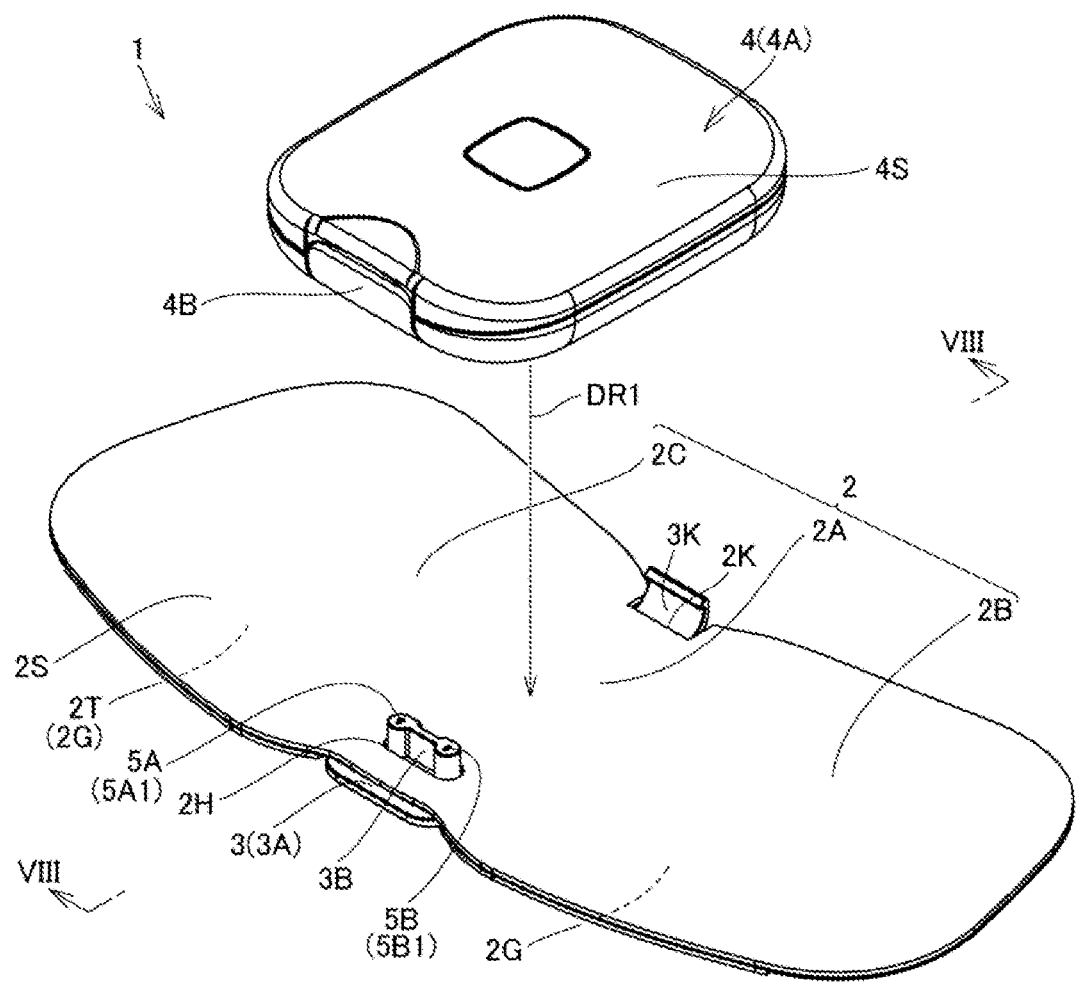
FIG. 2 is a perspective view illustrating a state in which a body 4 provided in the low frequency treatment device 1 according to the embodiment is assembled together with a holder 3 and a pad 2.
Figure 3:
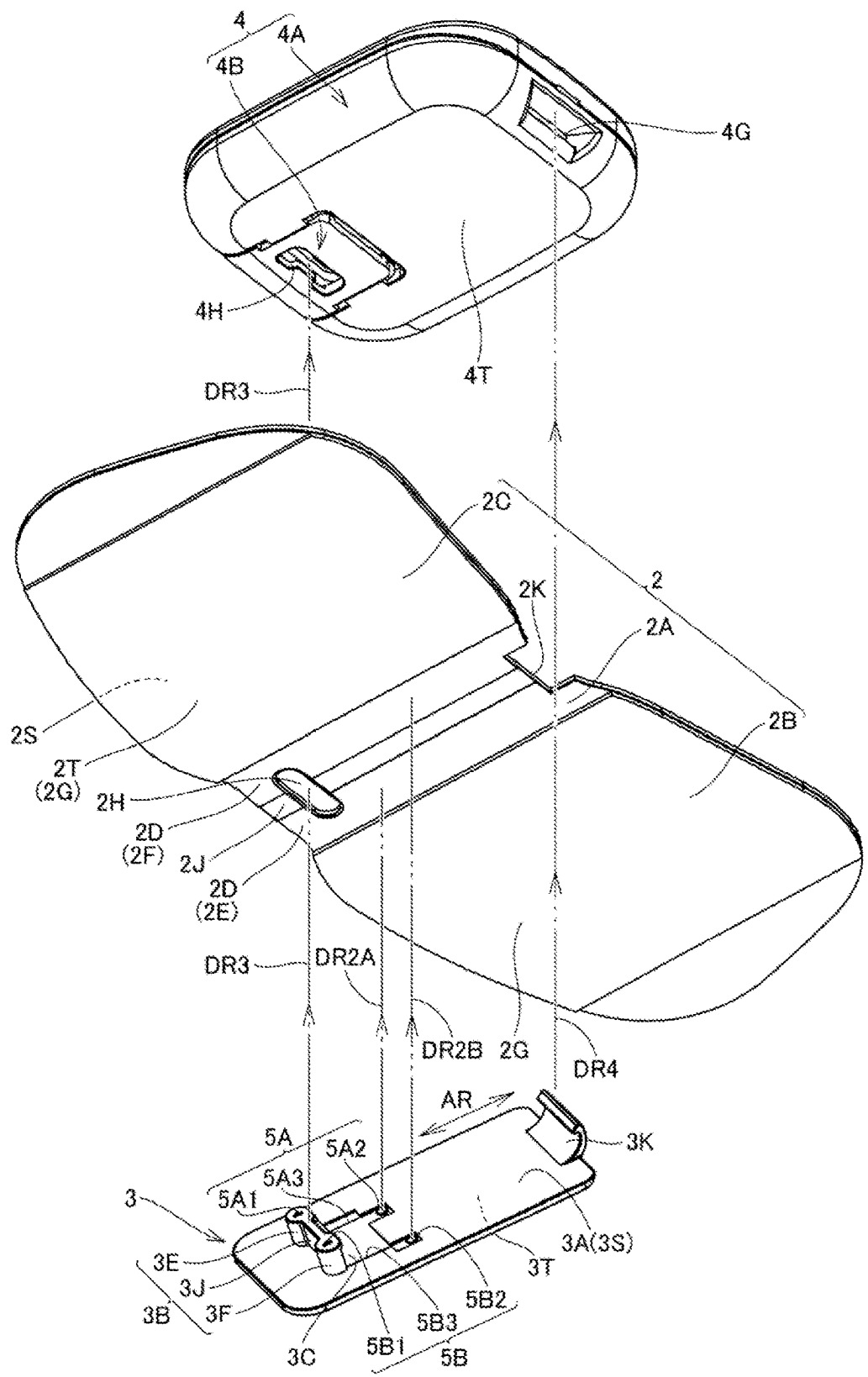
FIG. 3 is a perspective view illustrating a state in which the body 4, the pad 2, and the holder 3 provided in the low-frequency treatment device 1 according to the embodiment are separated from each other.

FIG. 1 is a perspective view illustrating the low-frequency treatment device 1. FIG. 2 is a perspective view illustrating a state in which a body 4 provided in the low-frequency treatment device 1 is assembled together with a holder 3 and a pad 2. FIG. 3 is a perspective view illustrating a state in which the body 4, the pad 2, and the holder 3 provided in the low-frequency treatment device 1 according to the embodiment are separated from each other.

Low-Frequency Treatment Device 1

As illustrated in FIGS. 1 to 3, the low-frequency treatment device 1 is a so-called cordless type low-frequency treatment device and includes the pad 2, the holder 3, the body 4, and wiring members 5A and 5B (FIG. 3).

Pad 2

The pad 2 is formed in a sheet-like shape and includes a front surface 2S and a rear surface 2T. The pad 2 is attached to the body of a user with the rear surface 2T of the pad 2 facing the body of the user. A conductive layer 2D (FIG. 3) is provided on the rear surface 2T (lower surface) of the pad 2. Conductive gel 2G (FIG. 3) is provided covering the conductive layer 2D. The conductive gel 2G is used to attach the pad 2 to the skin of the user. A low-frequency pulse current is supplied to the user via the conductive layer 2D and the conductive gel 2G.

The pad 2 has an attachment portion 2A (FIGS. 2 and 3) and treatment portions 2B and 2C. The attachment portion 2A is the portion supported by the holder 3 and is centrally located in the longitudinal direction of the pad 2. The treatment portions 2B and 2C are disposed on the outer sides of the attachment portion 2A in the longitudinal direction of the pad 2. An insulation region 2J that extends in the short direction of the pad 2 is formed on the rear surface 2T of the attachment portion 2A (see FIG. 3).

The insulation region 2J is formed, as viewed from the insulation region 2J, between one conductive layer 2D located on the treatment portion 2B side and another conductive layer 2D located on the treatment portion 2C side. The two conductive layers, namely, the one conductive layer 2D and the other conductive layer 2D are electrically isolated from each other by the presence of the insulation region 2J. The insulation region 2J is formed as such by virtue of a part in which the conductive layer 2D is not provided on the rear surface 2T of the pad 2.

Pad side electrodes 2E and 2F are formed on the rear surface 2T of the pad 2 (attachment portion 2A). Specifically, the conductive layer 2D located on the treatment portion 2B side of the insulation region 2J (the portion of the conductive layer 2D adjacent to the insulation region 2J) constitutes the pad side electrode 2E. The conductive layer 2D located on the treatment portion 2C side as viewed from the insulation region 2J (the portion of the conductive layer 2D adjacent to the insulation region 2J) constitutes the pad side electrode 2F (see FIG. 3).

The pad side electrodes 2E and 2F are located on the rear surface 2T of the attachment portion 2A of the pad 2 and have a shape that extends in the direction parallel with the short direction of the pad 2. The pad side electrodes 2E and 2F are formed to be electrically connected to body side electrodes 4DA and 4DB (see FIG. 7). Specifically, as will be described below with reference to FIG. 3 and FIGS. 5 to 7, the pad side electrode 2E is electrically connected to the body side electrode 4DA via the wiring member 5A, and the pad side electrode 2F is electrically connected to the body side electrode 4DB via the wiring member 5B.

Returning to FIG. 3, a through hole 2H is provided in the attachment portion 2A of the pad 2. The through hole 2H extends through the pad 2 from the front surface 2S to the rear surface 2T. The through hole 2H has an oval (substantially elliptical) shape that extends in the direction parallel with the longitudinal direction of the pad 2. The through hole 2H is formed to be orthogonal to the insulation region 2J.

An end portion of the through hole 2H on a first side in the longitudinal direction (the treatment portion 2B side) is located so as to cut into a portion of the pad side electrode 2E, and an end portion of the through hole 2H on a second side in the longitudinal direction (the treatment portion 2C side) is located so as to cut into a portion of the pad side electrode 2F. A protrusion portion 3B of the holder 3 described below is disposed inside the through hole 2H (see arrow DR3 in FIG. 3). In a state where the holder 3 is disposed on the rear surface 2T side of the pad 2, the protrusion portion 3B is disposed extending through the through hole 2H.

A cutout 2K (FIGS. 2 and 3) is formed in the peripheral edge of the attachment portion 2A of the pad 2. The cutout 2K is formed such that a portion of the peripheral edge of the attachment portion 2A of the pad 2 is recessed inward. In a configuration in which the through hole 2H is located on one side of the center position of the pad 2 in the short direction, the cutout 2K is located on the other side of the center position of the pad 2 in the short direction (opposite the through hole 2H). An engagement tab 3K (a second engagement portion) of the holder 3 described below is disposed inside the cutout 2K (see arrow DR4 in FIG. 3).

Holder 3

Figure 4:
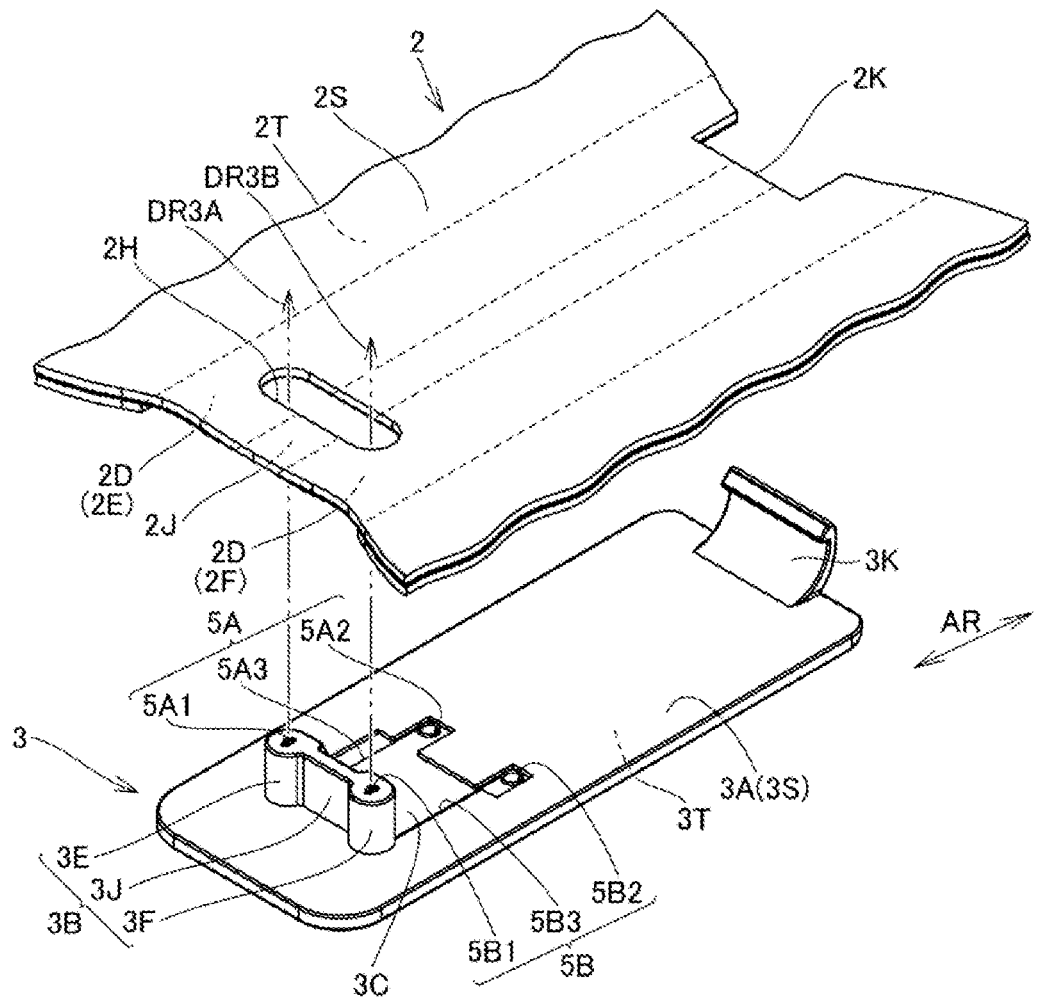
FIG. 4 is a perspective view illustrating a state in which the holder 3 provided in the low frequency treatment device 1 according to the embodiment is assembled together with the pad 2.
Figure 5:
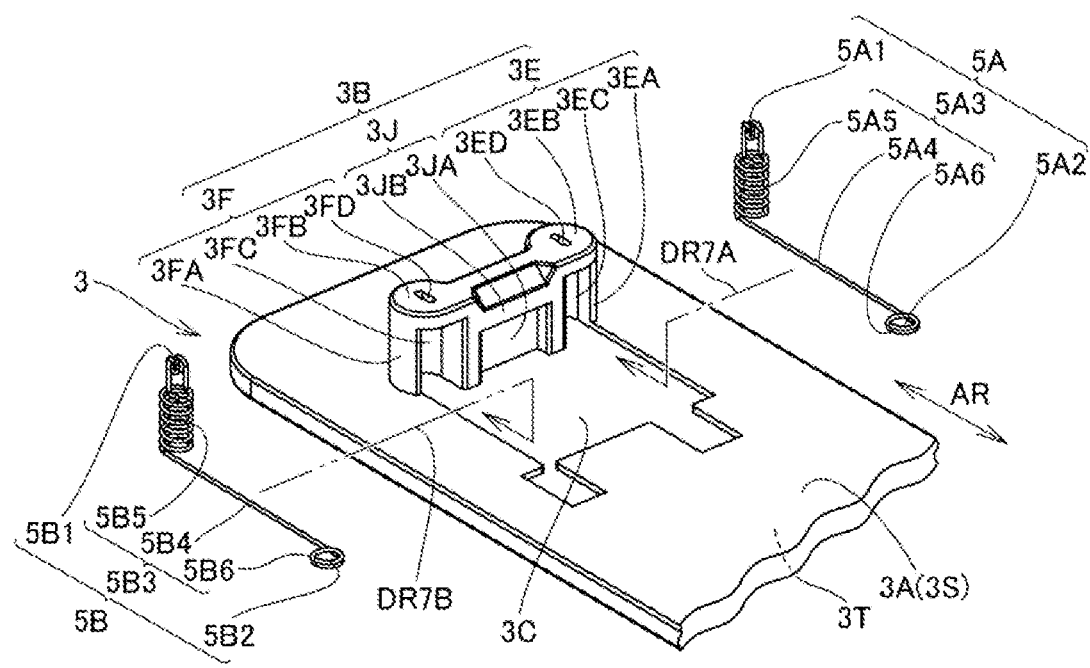
FIG. 5 is a perspective view illustrating a state in which wiring members 5A and 5B provided in the low frequency treatment device 1 according to the embodiment is assembled together with the holder 3.

FIG. 4 is a perspective view illustrating a state in which the holder 3 is assembled together with the pad 2. FIG. 5 is a perspective view illustrating a state in which the wiring members 5A and 5B are assembled together with the holder 3.

As illustrated in FIGS. 3 to 5, the holder 3 includes a plate-like portion 3A, the protrusion portion 3B, and the engagement tab 3K. The plate-like portion 3A includes a front surface 3S and a rear surface 3T. In the perspective view of FIG. 3, the pad 2 and the body 4 are illustrated as viewed from the side of the rear surface 2T and a lower surface 4T, and for the sake of convenience, the holder 3 is illustrated as viewed from the side of the front surface 3S. In FIG. 4, the pad 2 and the holder 3 are illustrated as viewed from the side of the front surface 2S and 3S.

The holder 3 is disposed on the rear surface 2T side of the pad 2, such that the front surface 3S of the plate-like portion 3A opposes the pad side electrodes 2E and 2F of the pad 2. A double-sided adhesive tape, glue, adhesive, or the like (adhesive portion) is disposed between the front surface 3S of the plate-like portion 3A and the rear surface 2T of the pad 2 as necessary, and the front surface 3S of the plate-like portion 3A and the rear surface 2T of the pad 2 may be joined to each other via an adhesive portion. The holder 3 is detachably attached to the body 4 so as to sandwich the pad 2 between the plate-like portion 3A of the holder 3 and the body 4. In an attached state, the pad 2 is held between the front surface 3S of the plate-like portion 3A and the body 4 (the lower surface 4T, i.e., the opposing surface).

The protrusion portion 3B is provided to project from the front surface 3S of the plate-like portion 3A. The protrusion portion 3B according to the present embodiment includes an engagement portion 3J (a first engagement portion) and projection portions 3E and 3F. The engagement portion 3J and the projection portions 3E and 3F are integrally formed in the present embodiment, but in another configuration, some or all of the engagement portion 3J, the projection portion 3E, and the projection portion 3F may be configured separately, and may be formed independently on the front surface 3S of the plate-like portion 3A.

In a plan view of the protrusion portion 3B, the external shape of the protrusion portion 3B corresponds to the shape of the inner peripheral edge of the through hole 2H provided in the pad 2. The protrusion portion 3B of the holder 3 (the engagement portion 3J and the projection portions 3E and 3F) are disposed inside the through hole 2H (see arrows DR3A and DR3B in FIG. 4). By fitting the inner peripheral edge of the through hole 2H provided in the pad 2 to the protrusion portion 3B, the pad 2 can be easily positioned with respect to the holder 3.

The pad 2 is a consumable item, and the pad 2 can be detachably attached to the body 4, thus allowing replacement of the pad 2. In the present embodiment, the holder 3 holds the pad 2 such that the holder 3 and the pad 2 are integrated, and the body 4 is configured to be detachably attached to the pad 2 and the holder 3. The pad 2 can be replaced together with the holder 3, or it is also possible to reuse the holder 3 as necessary.

Projection Portions 3E and 3F of Holder 3

The projection portion 3E (see FIG. 5) includes a vertical wall portion 3EA, a top surface portion 3EB, a receiving portion 3EC, and an insertion hole 3ED. The vertical wall portion 3EA has a shape like a curved plate (a cylinder with a portion removed) and stands upright from the front surface 3S of the plate-like portion 3A. The receiving portion 3EC is formed inside the vertical wall portion 3EA. Assuming that the side on which the projection portion 3E is provided is defined as a first side with respect to a longitudinal direction AR of the holder 3 (plate-like portion 3A), the receiving portion 3EC is open facing a second side (the side where the engagement tab 3K is located) in the longitudinal direction AR of the holder 3. The top surface portion 3EB has a disc-like shape and closes the top end of the vertical wall portion 3EA in the upright direction. The insertion hole 3ED is centrally formed at the center of the top surface portion 3EB.

The projection portion 3F (see FIG. 5) includes a vertical wall portion 3FA, a top surface portion 3FB, a receiving portion 3FC, and an insertion hole 3FD. The vertical wall portion 3FA has a shape like a curved plate (a cylinder with a portion removed) and stands upright from the front surface 3S of the plate-like portion 3A. The receiving portion 3FC is formed inside the vertical wall portion 3FA. Assuming that the side on which the projection portion 3F is provided is defined as the first side with respect to a longitudinal direction AR of the holder 3 (plate-like portion 3A), the receiving portion 3FC is open facing the second side (the side where the engagement tab 3K is located) in the longitudinal direction AR of the holder 3. The top surface portion 3FB has a disc-like shape and closes the top end of the vertical wall portion 3FA in the upright direction. The insertion hole 3FD is formed at the center of the top surface portion 3FB.

Engagement Portion 3J of Holder 3

The engagement portion 3J, that is, the first engagement portion, includes an upright portion 3JA and an overhang portion 3JB. The upright portion 3JA has a shape like a table and stands upright from the front surface 3S of the plate-like portion 3A. The upright portion 3JA is formed extending in a direction orthogonal to the longitudinal direction AR of the holder 3 (plate-like portion 3A). The overhang portion 3JB is formed to project toward the second side (the side where the engagement tab 3K is located) in the longitudinal direction AR of the holder 3 from the top end of the upright portion 3JA in the upright direction.

In a cross-sectional view of the engagement portion 3J (see FIG. 8), the upright portion 3JA and the overhang portion 3JB have a substantially L-like shape, and a recess is formed inside the engagement portion 3J (the side at which the engagement tab 3K is located as viewed from the engagement portion 3J). As will be described in detail below, by engaging and disengaging a projection 4F provided on the body 4 (an operation piece 4B) with/from the recess (see FIGS. 9 and 10), the body 4 and the holder 3 can be engaged together or disengaged.

Step Region 3C of Holder 3

As a preferable configuration example, a step region 3C is provided to be recessed from the front surface 3S of the plate-like portion 3A of the holder 3 of the present embodiment. The step region 3C is formed to extend toward the second side (the side at which the engagement tab 3K is located) in the longitudinal direction AR of the holder 3 from the position at which the protrusion portion 3B is provided.

The wiring member 5A and 5B described below are disposed in the step region 3C (see arrows DR7A and DR1B in FIG. 5). Although the step region 3C is not required as part of the configuration, by providing the step region 3C, the occurrence of misalignment of the wiring members 5A and 5B can be suppressed, and by providing the wiring members 5A and 5B, the occurrence of unnecessary wrinkles and the like in the pad 2 can be suppressed.

Engagement Tab 3K of Holder 3

As a preferable configuration example, the holder 3 includes the engagement tab 3K (the second engagement portion). The engagement tab 3K is provided on the side opposite to the side on which the protrusion portion 3B (the engagement portion 3J, that is, the first engagement portion) is provided, with respect to the longitudinal direction of the plate-like portion 3A. The engagement tab 3K is disposed inside the cutout 2K provided in the pad 2. The engagement tab 3K is not required as part of the configuration, but can engage with a recess portion 4G of the body 4 (a case body 4A) described below.

Body 4

Figure 6:
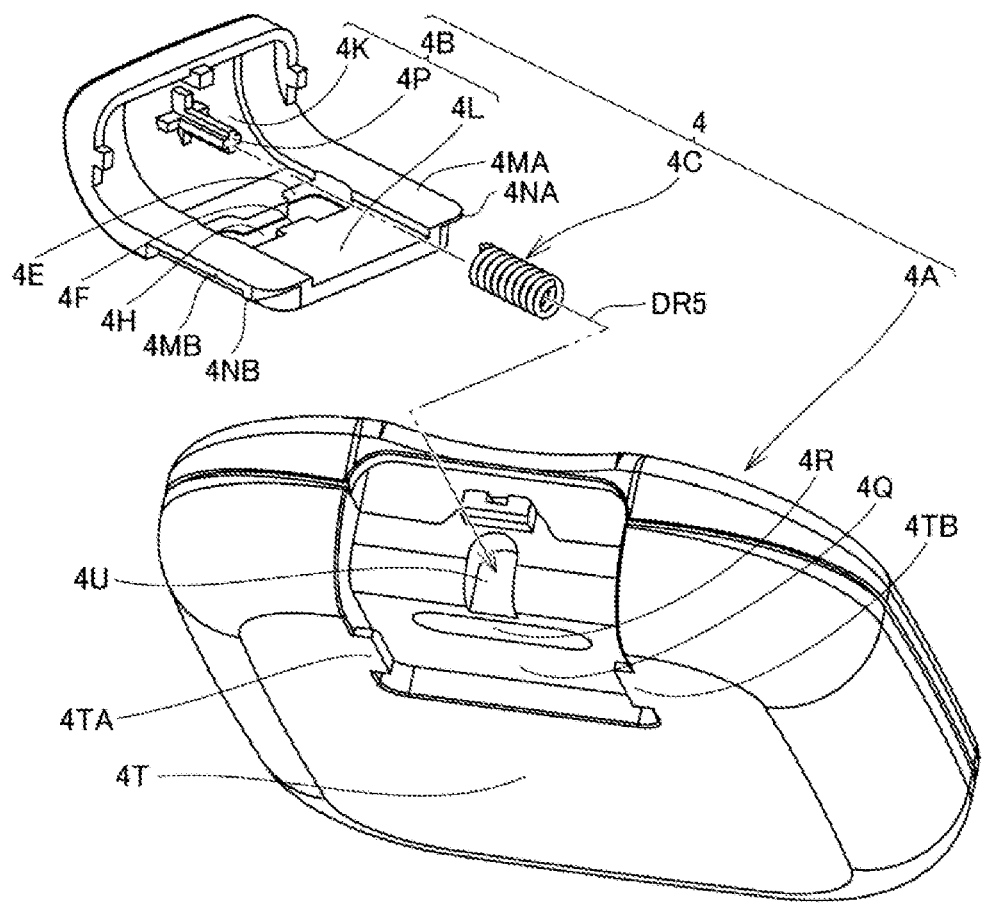
FIG. 6 is a first perspective view illustrating a state in which the body 4 provided in the low-frequency treatment device 1 according to the embodiment is disassembled (a state in which an operation piece 4B and a bias portion 4C are detached from a case body 4A).
Figure 7:
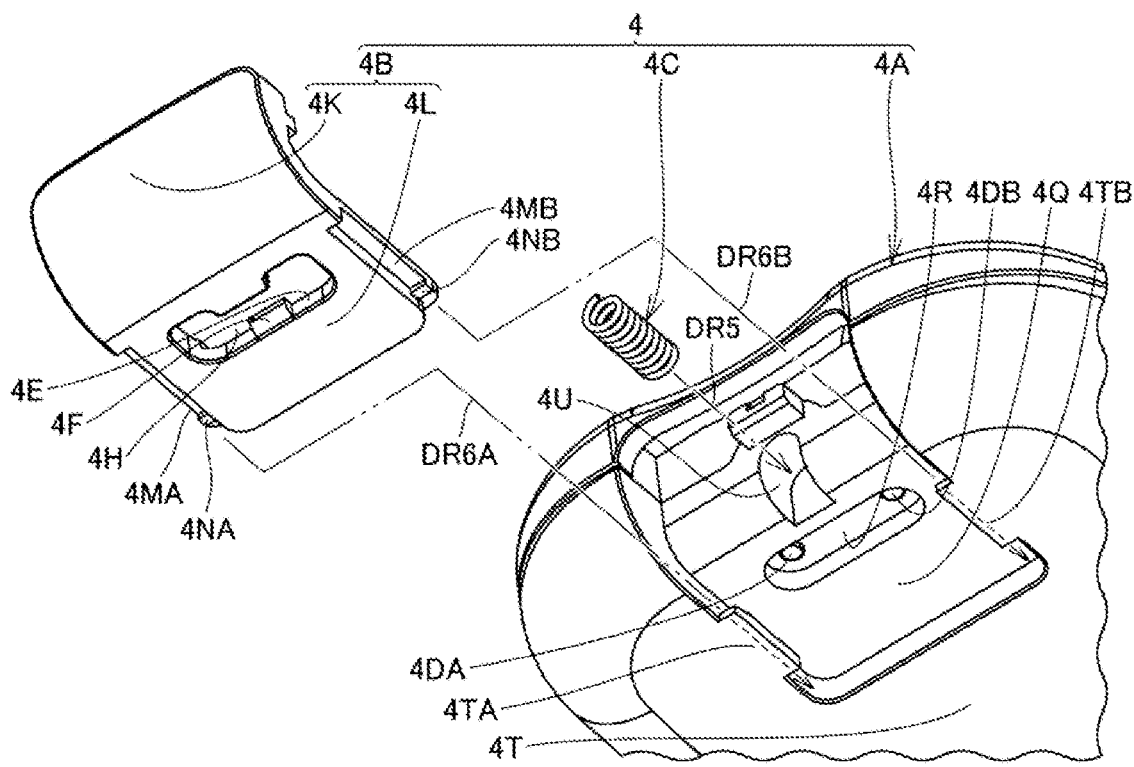
FIG. 7 is a second perspective view illustrating a state in which the body 4 provided in the low-frequency treatment device 1 according to the embodiment is disassembled (a state in which the operation piece 4B and the bias portion 4C are detached from the case body 4A).

FIG. 6 is a first perspective view illustrating a state in which the body 4 is disassembled (a state in which the operation piece 4B and the bias portion 4C are detached from the case body 4A). FIG. 7 is a second perspective view illustrating a state in which the body 4 is disassembled (a state in which the operation piece 4B and a bias portion 4C are detached from the case body 4A). As illustrated in FIGS. 1 to 3, and FIGS. 6 and 7, the body 4 includes the case body 4A, the operation piece 4B, and the bias portion 4C (FIGS. 6 and 7).

Case Body 4A

The case body 4A has a substantially rectangular parallelepiped shape, and has a battery, various control devices for generating low-frequency pulse current, and the like (not illustrated) that are built in the case body 4A. The case body 4A includes an upper surface 4S and the lower surface 4T (opposite surface). The body 4 is disposed such that the lower surface 4T (opposite surface) of the case body 4A opposes the front surface 3S of the holder 3. The body 4 is detachably attached to the holder 3 so as to sandwich the pad 2 (attachment portion 2A) between the lower surface 4T of the case body 4A and the front surface 3S of the holder 3 (arrow DR1 in FIG. 2).

The operation piece 4B is provided in a manner allowing for sliding movement on one side in the longitudinal direction of the case body 4A. The recess portion 4G is provided on the other side in the longitudinal direction of the case body 4A. As described above, the engagement tab 3K provided on the holder 3 can engage with the recess portion 4G. The body side electrodes 4DA and 4DB (FIG. 7) are provided on the lower surface 4T side of the case body 4A.

Specifically, a housing portion 4Q is provided to be recessed from the lower surface 4T of the case body 4A. In the housing portion 4Q, recessed portions 4U and 4R are formed to be recessed inward from the surface of the housing portion 4Q. The housing portion 4Q extends in a substantially J-like shape in a cross-sectional view from one end in the longitudinal direction of the case body 4A toward the lower surface 4T side. The housing portion 4Q is formed such that a portion of the outer surface of the case body 4A is recessed inward.

The recessed portion 4U is provided to be recessed in a portion of the housing portion 4Q located on the side of one end of the case body 4A in the longitudinal direction. The recessed portion 4U extends in the direction parallel with the longitudinal direction of the case body 4A, and a bias portion 4C is disposed inside the recessed portion 4U (arrow DR5). The bias portion 4C biases the operation piece 4B such that the operation piece 4B moves from the side of a released position (a released position 4B2 described below with reference to FIG. 10) toward the side of an engaged position (an engaged position 4B1 described below with reference to FIG. 9).

The recessed portion 4R is provided to be recessed in a portion of the housing portion 4Q parallel with the lower surface 4T. The body side electrodes 4DA and 4DB are arranged inside the recessed portion 4R (on the bottom surface of the recessed portion 4R) (see FIG. 7). The body side electrodes 4DA and 4DB are constituted by an end portion of a metal terminal and are electrically connected to a control device (not illustrated) built into the body 4 (case body 4A) (see reference numeral 8A in FIG. 8).

As illustrated in FIGS. 6 and 7, a pair of projection pieces 4TA and 4TB are also provided on the lower surface 4T of the case body 4A. The projection pieces 4TA and 4TB oppose the recessed portion 4R with a gap therebetween. The projection pieces 4TA and 4TB extend in the direction parallel with the lower surface 4T of the case body 4A. The gap is provided between the projection piece 4TA and the recessed portion 4R, and between the projection piece 4TB and the recessed portion 4R for inserting insertion pieces 4MA and 4MB of the operation piece 4B into the gap.

Operation Piece 4B

The operation piece 4B is disposed inside the housing portion 4Q of the case body 4A in a manner allowing for sliding movement in the longitudinal direction of the case body 4A. Specifically, the operation piece 4B includes a curved portion 4K, a flat portion 4L, and a projection 4P. These overall form a shape that corresponds to the shape of the housing portion 4Q.

The flat portion 4L of the operation piece 4B is disposed to oppose the portion of the housing portion 4Q of the case body 4A that is parallel with the lower surface 4T. The insertion pieces 4MA and 4MB having a thin plate-like shape are provided on both of the left side and right side of the flat portion 4L. Protrusion portions 4NA and 4NB are respectively provided on the end sides of the insertion pieces 4MA and 4MB in the insertion direction.

The flat portion 4L of the operation piece 4B is assembled together with the case body 4A by the insertion piece 4MA being inserted between the lower surface of the housing portion 4Q and the projection piece 4TA (arrow DR6A in FIG. 7) and the insertion piece 4MB being inserted between the lower surface of the housing portion 4Q and the projection piece 4TB (arrow DR6B in FIG. 7).

The protrusion portion 4NA provided on the end of the insertion piece 4MA of the operation piece 4B is locked to the end portion of the projection piece 4TA provided on the case body 4A, and the protrusion portion 4NB provided on the end of the insertion piece 4MB of the operation piece 4B is locked to the end portion of the projection piece 4TB provided on the case body 4A. As described above, the bias portion 4C biases the operation piece 4B such that the operation piece 4B moves from the side of a released position (the released position 4B2 described below with reference to FIG. 10) toward the side of an engaged position (the engaged position 4B1 described below with reference to FIG. 9).

By the protrusion portions 4NA and 4NB locked to the ends of the insertion pieces 4MA and 4MB, the operation piece 4B is prevented from falling out from the case body 4A. This configuration allows the operation piece 4B to move in a sliding movement manner, with respect to the case body 4A, between a released position (the released position 4B2 described below with reference to FIG. 10) and an engaged position (the engaged position 4B1 described below with reference to FIG. 9).

The curved portion 4K of the operation piece 4B is connected to the back end portion of the flat portion 4L in the insertion direction, and the projection 4P is provided on the inside of the curved portion 4K. The bias portion 4C according to the present embodiment has the shape of a coil spring and is disposed to be surrounding the periphery of the projection 4P. In a state in which the operation piece 4B is assembled together with the case body 4A, the bias portion 4C is disposed inside the recessed portion 4U provided in the case body 4A (arrow DR5).

An insertion opening 4H is formed in the flat portion 4L of the operation piece 4B. The insertion opening 4H extends through the flat portion 4L in the thickness direction thereof. The projection 4F is formed on an inner peripheral edge 4E defining the insertion opening 4H of the operation piece 4B (flat portion 4L). When the insertion opening 4H is viewed in a plan view, the shape of the inner peripheral edge 4E of the insertion opening 4H corresponds to the outer shape of the protrusion portion 3B provided on the holder 3. The protrusion portion 3B of the holder 3 (the engagement portion 3J and the projection portions 3E and 3F) are disposed inside the insertion opening 4H (see arrow DR3 in FIG. 3).

When the entire of the body 4 is viewed, the insertion opening 4H is located on the lower surface 4T (opposite surface) of the body 4, and in a state in which the operation piece 4B is assembled together with the case body 4A, the body side electrodes 4DA and 4DB are located inside the insertion opening 4H. In other words, the body side electrodes 4DA and 4DB are disposed in a manner allowing them to be exposed through the insertion opening 4H of the operation piece 4B. As described above with reference to FIGS. 3 to 5, the pad side electrode 2E is electrically connected to the body side electrode 4DA (FIG. 7) via the wiring member 5A, and the pad side electrode 2F is electrically connected to the body side electrode 4DB (FIG. 7) via the wiring member 5B.

Wiring Member 5A

The wiring member 5A includes a first end portion 5A1, a second end portion 5A2, and a conductive portion 5A3, and is composed by a thin wire member having electrical conductivity throughout. The first end portion 5A1 is a portion of the wiring member 5A connected to the body side electrode 4DA (FIG. 7), and the second end portion 5A2 is a portion of the wiring member 5A connected to the pad side electrode 2E (arrow DR2A in FIG. 3).

The conductive portion 5A3 of the wiring member 5A is a portion that conducts electricity between the first end portion 5A1 and the second end portion 5A2. A portion of the conductive portion 5A3 (specifically, an elastic portion 5A5 of the conductive portion 5A3) is disposed to pass through the through hole 2H of the pad 2 (FIG. 4). The conductive portion 5A3 of the present embodiment includes a linear portion 5A4 and elastic portions 5A5 and 5A6. The elastic portion 5A5 (a first elastic portion) is provided at a position on the first end portion 5A1 side when viewed from the linear portion 5A4 and is formed continuously from one end of the linear portion 5A4. The elastic portion 5A6 (a second elastic portion) is provided at a position on the second end portion 5A2 side when viewed from the linear portion 5A4 and is formed continuously from the other end of the linear portion 5A4. In the present embodiment, the elastic portions 5A5 and 5A6 have the shape of a coil spring.

The elastic portion 5A5 is disposed inside the projection portion 3E (the vertical wall portion 3EA) provided on the holder 3, that is, inside the receiving portion 3EC. The elastic portion 5A5 of the conducting portion 5A3 (a portion of the conductive portion 5A3) is disposed so as to pass through the through hole 2H of the pad 2 and is held by the projection portion 3E provided on the holder 3. The first end portion 5A1 of the wiring member 5A protrudes from the insertion hole 3ED provided in the projection portion 3E of the holder 3 (FIG. 5), and when the holder 3 is assembled together with the body 4, the first end portion 5A1 can be brought into contact with the body side electrode 4DA by the biasing force of the elastic portion 5A5.

The linear portion 5A4 and the elastic portion 5A6 of the wiring member 5A are mounted on the step region 3C of the holder 3. By providing the step region 3C, the occurrence of misalignment of the wiring member 5A can be suppressed, and by providing the wiring member 5A, the occurrence of unnecessary wrinkles and the like in the pad 2 can be suppressed. The elastic portion 5A6 is located on the side opposite to the elastic portion 5A5 as viewed from the linear portion 5A4, and when the holder 3 is assembled together with the body 4, the second end portion 5A2 can be brought into contact with the pad side electrode 2E by the biasing force of the elastic portion 5A6.

Wiring Member 5B

The wiring member 5B includes a first end portion 5B1, a second end portion 5B2, and a conductive portion 5B3, and is composed by a thin wire member having electrical conductivity throughout. The first end portion 5B1 is a portion of the wiring member 5B connected to the body side electrode 4DB (FIG. 7), and the second end portion 5B2 is a portion of the wiring member 5B connected to the pad side electrode 2F (arrow DR2B in FIG. 3).

The conductive portion 5B3 of the wiring member 5B is a portion that conducts electricity between the first end portion 5B1 and the second end portion 5B2. A portion of the conductive portion 5B3 (specifically, an elastic portion 5B5 of the conductive portion 5B3) is disposed so as to pass through the through hole 2H of the pad 2 (FIG. 4). The conductive portion 5B3 of the present embodiment includes a linear portion 5B4 and elastic portions 5B5 and 5B6. The elastic portion 5B5 (a first elastic portion) is provided at a position on the first end portion 5B1 side when viewed from the linear portion 5B4 and is formed continuously from one end of the linear portion 5B4. The elastic portion 5B6 (a second elastic portion) is provided at a position on the second end portion 5B2 side when viewed from the linear portion 5B4 and is formed continuously from the other end of the linear portion 5B4. In the present embodiment, the elastic portions 5B5 and 5B6 each have the shape of a coil spring.

The elastic portion 5B5 is disposed inside the projection portion 3F (the vertical wall portion 3FA) provided on the holder 3, that is, inside the receiving portion 3FC. The elastic portion 5B5 of the conducting portion 5B3 (a portion of the conductive portion 5B3) is disposed so as to pass through the through hole 2H of the pad 2 and is held by the projection portion 3F provided on the holder 3. The first end portion 5B1 of the wiring member 5B protrudes from the insertion hole 3FD provided in the projection portion 3F of the holder 3 (FIG. 5), and when the holder 3 is assembled together with the body 4, the first end portion 5B1 can be brought into contact with the body side electrode 4DB by the biasing force of the elastic portion 5B5.

The linear portion 5B4 and the elastic portion 5B6 of the wiring member 5B are mounted on the step region 3C of the holder 3. By providing the step region 3C, the occurrence of misalignment of the wiring member 5B can be suppressed, and by providing the wiring member 5B, the occurrence of unnecessary wrinkles and the like in the pad 2 can be suppressed. The elastic portion 5B6 is located on the side opposite to the elastic portion 5B5 as viewed from the linear portion 5B4, and when the holder 3 is assembled together with the body 4, the second end portion 5B2 can be brought into contact with the pad side electrode 2F by the biasing force of the elastic portion 5B6.

Assembly of Holder 3 and Pad 2 to the Body 4

Figure 8:
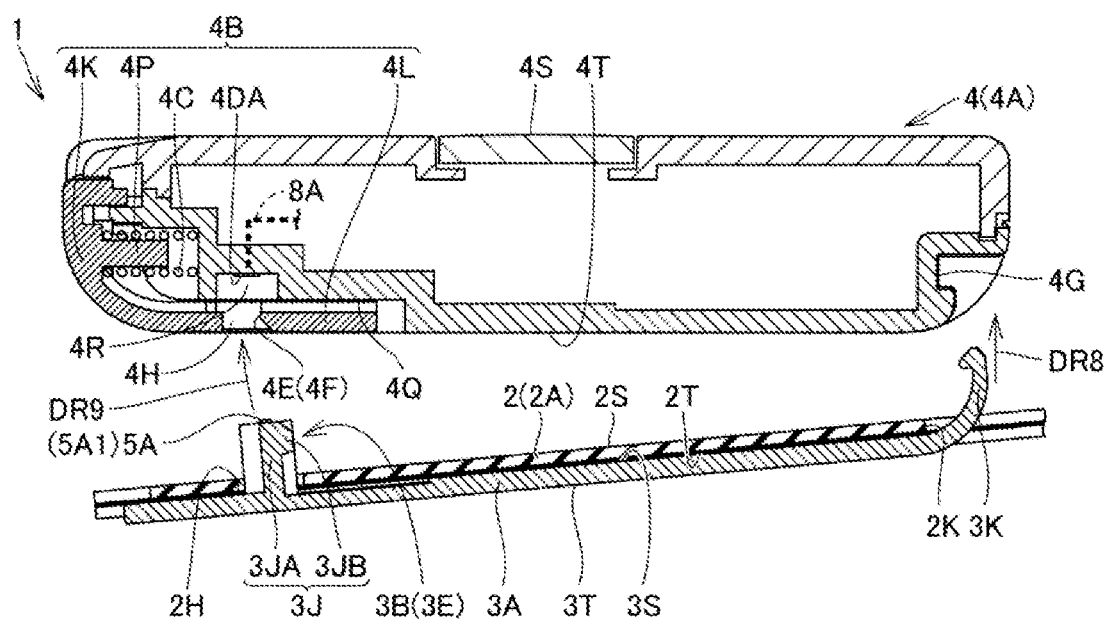
FIG. 8 is a cross-sectional view along line VIII-VIII in the direction of the arrow in FIG. 2 and illustrates a state in which the holder 3 and the pad 2 provided in the low frequency treatment device 1 according to the embodiment are assembled together with the body 4.

FIG. 8 is a cross-sectional view along line VIII-VIII in the direction of the arrow in FIG. 2 and illustrates a state in which the holder 3 and the pad 2 provided in the low frequency treatment device 1 according to the embodiment are assembled together with the body 4. When assembling the holder 3 and the pad 2 together with the body 4, first, the engagement tab 3K of the holder 3 is engaged with the recess portion 4G of the body 4 (arrow DR8). Thereafter, the protrusion portion 3B of the holder 3 is inserted into the insertion opening 4H (arrow DR9).

Figure 9:
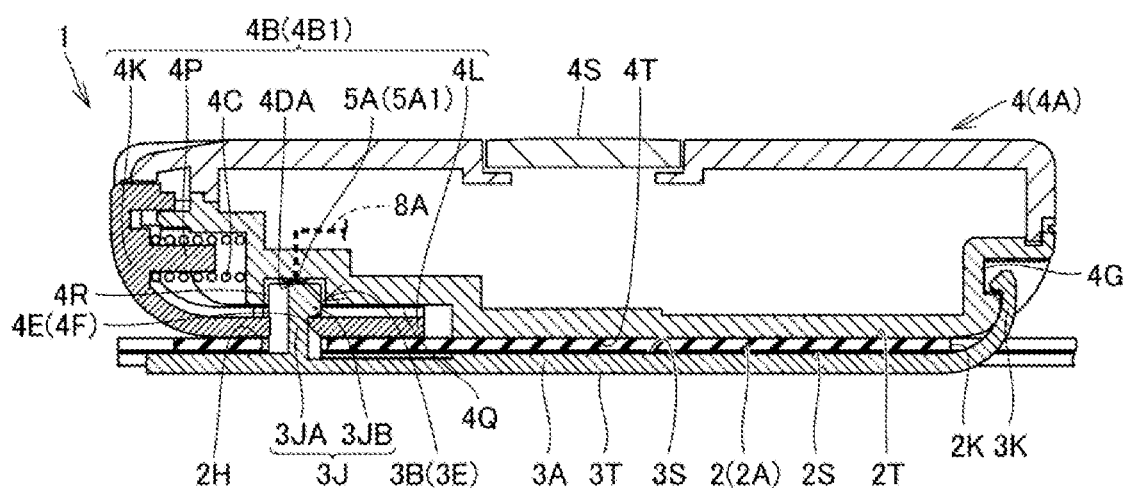
FIG. 9 is a cross-sectional view of the low-frequency treatment device 1 according to the embodiment, and illustrates a state in which the operation piece 4B is disposed at the engaged position 4B1.

Referring to FIG. 9, in a state prior to insertion, the operation piece 4B is disposed in the engaged position 4B1 by the biasing force of the bias portion 4C. The operation piece 4B is in a state of being slightly separated from the case body 4A. By inserting the projection portion 3E of the holder 3 into the insertion opening 4H, the operation piece 4B is slightly displaced toward the case body 4A (to the right in FIG. 9) against the biasing force of the bias portion 4C. When the protrusion portion 3B of the projection portion 3E is disposed beyond the inner peripheral edge 4E (projection 4F) defining the insertion opening 4H, the operation piece 4B returns to the engagement position 4B1 by using the biasing force of the bias portion 4C.

The protrusion portion 3B of the projection portion 3E and the inner peripheral edge 4E (projection 4F) defining the insertion opening 4H engage with each other. The body 4 and the holder 3 are assembled together. In this state, the projection portion 3E is inserted into the insertion opening 4H of the operation piece 4B, and the first end portions 5A1 and 5B1 of the wiring members 5A and 5B respectively abut against the body side electrodes 4DA and 4DB, thus causing conductivity to be established between the first end portion 5A1 of the wiring member 5A and the body side electrode 4DA, and between the first end portion 5B1 of the wiring member 5B and the body side electrode 4DB. The pad side electrode 2E is electrically connected to the body side electrode 4DA via the wiring member 5A, and the pad side electrode 2F is electrically connected to the body side electrode 4DB via the wiring member 5B.

Figure 10:
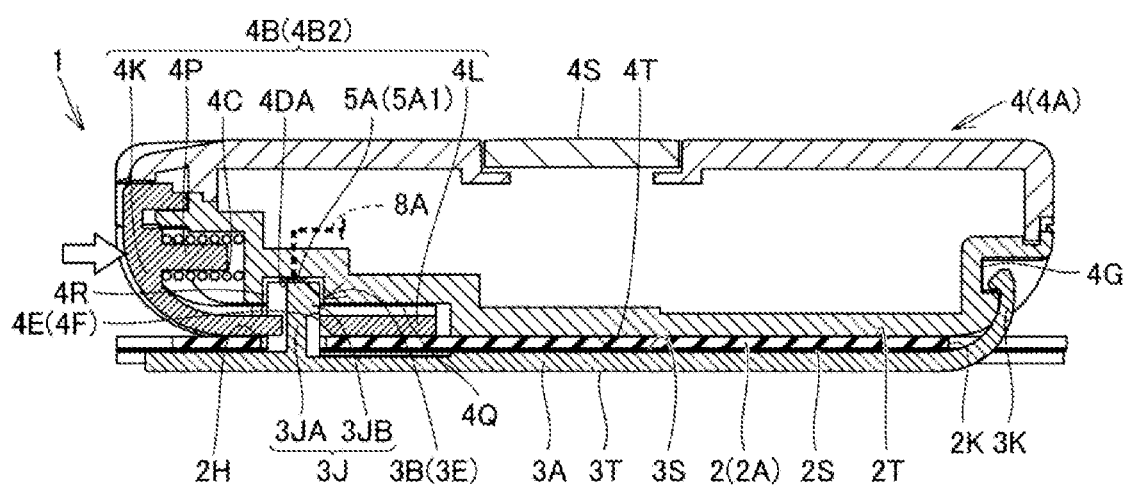
FIG. 10 is a cross-sectional view of the low-frequency treatment device 1 according to the embodiment, and illustrates a state in which the operation piece 4B is disposed at the released position 4B2.

With reference to FIG. 10, when an external force is applied to the operation piece 4B, the operation piece 4B is disposed in the released position 4B2 resisting against the biasing force of the bias portion 4C. Thus, the engagement between the protrusion portion 3B of the projection portion 3E and the inner peripheral edge 4E (projection 4F) defining the insertion opening 4H is released, allowing the holder 3 to be removed from the body 4.

Function and Effect

In the present embodiment, the through hole 2H is provided in the pad 2, and the conductive portions 5A3 and 5B3 (more specifically, the elastic portions 5A5 and 5B5) of the wiring members 5A and 5B are disposed so as to pass through the through hole 2H. The wiring members 5A and 5B are able to conduct electricity between the body side electrodes 4DA, 4DB and the pad side electrodes 2E, 2F at a position inward from the outer peripheral edge of the pad 2. This allows the low-frequency treatment device to be made compact.

In contrast, in the low-frequency treatment device described in Patent Document 1 (JP H06-339531 A), when the pad is viewed in a plan view, the pair of connection terminals provided on the upper half portion and the pair of connection terminals provided on the lower half portion are connected to each other at a position outward from a peripheral edge of the pad (see FIG. 4 of Patent Document 1). This configuration makes it difficult to reduce the size of the upper half portion (the body) and the lower half portion (the holder), and thus makes it difficult to reduce the overall size of the low-frequency treatment device.

Furthermore, in the present embodiment, the operation piece 4B is selectively disposed in the engaged position 4B1 and the released position 4B2 by sliding movement of the operation piece 4B. In a state in which the operation piece 4B is disposed at the engaged position 4B1, the protrusion portion 3B of the projection portion 3E and the inner peripheral edge 4E (projection 4F) defining the insertion opening 4H engage with each other. According to this configuration, the holder 3 and the body 4 can be reliably coupled together. Additionally, when an external force is applied to the operation piece 4B, the operation piece 4B is disposed at the released position 4B2 resisting against the biasing force of the bias portion 4C. This allows the holder 3 to be easily removed from the body 4.

In contrast, in the low-frequency treatment device described in Patent Document 1 (JP H06-339531 A), the fitting structure is such that, when the projection provided in the lower half portion (the holder) is inserted into the recess portion provided in the upper half portion (the body), a portion of the lower half portion (the vertical wall portion on which the projection is formed) elastically deforms and the elastic deformation is relaxed to achieve the fitting. In this configuration, the lower half portion (the holder) may not be easily removed from the upper half portion (the body) depending on the elastic deformation and the relaxing deformation of the vertical wall portion with the projection.

Modified Example

Figure 11:
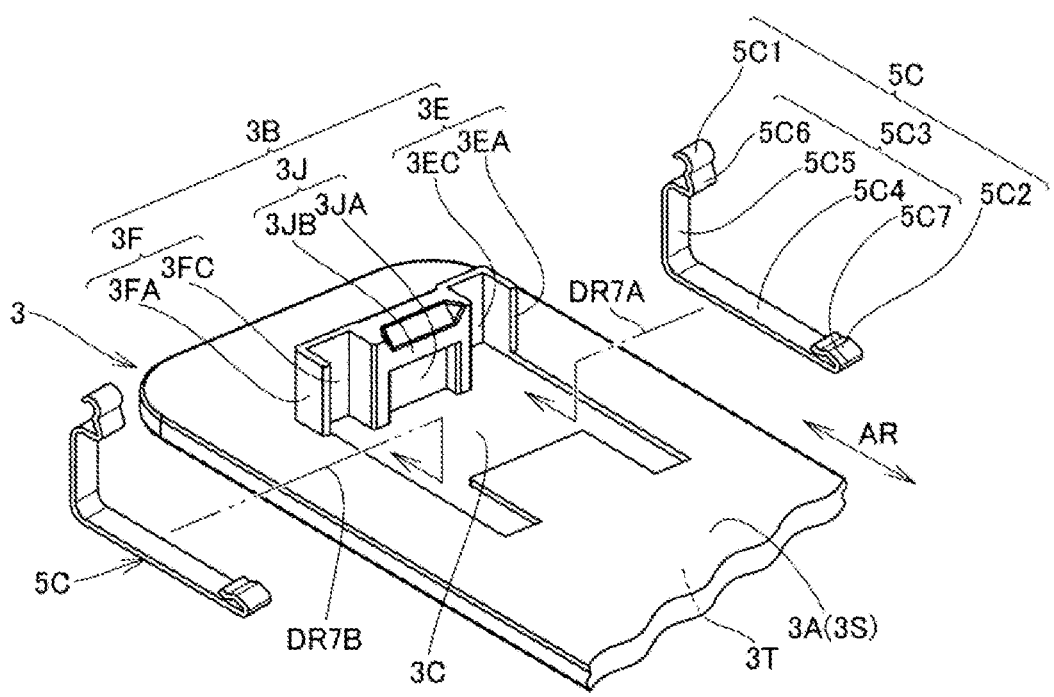
FIG. 11 is a perspective view illustrating a state in which a wiring member 5C provided in a low frequency treatment device according to a modified example is assembled together with the holder 3.

Referring to FIG. 11, instead of the wiring members 5A and 5B (see FIG. 5 and the like) in the above-described embodiment, one wiring member 5C and another wiring member 5C as illustrated in FIG. 11 may be used.

The wiring member 5C includes a first end portion 5C1, a second end portion 5C2, and a conductive portion 5C3, and is composed by a thin wire member having electrical conductivity throughout. The first end portion 5C1 is a portion of the wiring member 5C connected to the body side electrode 4DA (FIG. 7) (or the body side electrode 4DB), and the second end portion 5C2 is a portion of the wiring member 5C connected to the pad side electrode 2E (FIG. 3) (or the pad side electrode 2F).

The conductive portion 5C3 of the wiring member 5C is a portion that conducts electricity between the first end portion 5C1 and the second end portion 5C2. A portion of the conductive portion 5C3 (specifically, an upright portion 5C5 of the conductive portion 5C3) is disposed so as to pass through the through hole 2H of the pad 2 (FIG. 4). The conductive portion 5C3 of the wiring member 5C includes a linear portion 5C4, the upright portion 5C5, and elastic portions 5C6 and 5C7. The upright portion 5C5 is provided at a position on the first end portion 5C1 side when viewed from the linear portion 5C4 and is formed to bend substantially at a right angle from one end of the linear portion 5C4.

The elastic portion 5C6 (the first elastic portion) is provided at a position on the first end portion 5C1 when viewed from the upright portion 5C5. The elastic portion 5C6 is positioned between the upright portion 5C5 and the first end portion 5C1, is formed in a leaf spring shape so as to bend in a substantially V-like shape or a substantially U-like shape from one end of the upright portion 5C5, and is continuous with the first end portion 5C1.

The elastic portion 5C7 (the second elastic portion) is provided at a position on the second end portion 5C2 side when viewed from the linear portion 5C4. The elastic portion 5C7 is positioned between the linear portion 5C4 and the second end portion 5C2, is formed in a leaf spring shape to bend in a substantially V-like shape or a substantially U-like shape from the other end of the linear portion 5C4, and is continuous with the second end portion 5C2.

With regard to the wiring member 5C located on the projection portion 3E side of the holder 3, the upright portion 5C5 is disposed inside the projection portion 3E (the vertical wall portion 3EA) provided on the holder 3, that is, inside the receiving portion 3EC. The upright portion 5C5 of the conducting portion 5C3 (a portion of the conductive portion 5C3) is disposed so as to pass through the through hole 2H (FIG. 4) of the pad 2 and is held by the projection portion 3E provided on the holder 3. The first end portion 5C1 of the wiring member 5C, when the holder 3 is assembled together with the body 4, the first end portion 5C1 can be brought into contact with the body side electrode 4DA by the biasing force of the elastic portion 5C6. The linear portion 5C4 of the wiring member 5C is mounted on the step region 3C of the holder 3. By providing the step region 3C, the occurrence of misalignment of the wiring member 5C can be suppressed, and by providing the wiring member 5C, the occurrence of unnecessary wrinkles and the like in the pad 2 can be suppressed. The elastic portion 5C7 is located on the side opposite to the elastic portion 5C6 as viewed from the linear portion 5C4, and when the holder 3 is assembled together with the body 4, the second end portion 5C2 can be brought into contact with the pad side electrode 2E by the biasing force of the elastic portion 5C7.

With regard to the wiring member 5C located on the projection portion 3F side of the holder 3, the upright portion 5C5 is disposed inside the projection portion 3F (the vertical wall portion 3FA) provided on the holder 3, that is, inside the receiving portion 3FC. The upright portion 5C5 of the conducting portion 5C3 (a portion of the conductive portion 5C3) is disposed so as to pass through the through hole 2H (FIG. 4) of the pad 2 and is held by the projection portion 3F provided on the holder 3. The first end portion 5C1 of the wiring member 5C, when the holder 3 is assembled together with the body 4, the first end portion 5C1 can be brought into contact with the body side electrode 4DB by the biasing force of the elastic portion 5C6. The linear portion 5C4 of the wiring member 5C is mounted on the step region 3C of the holder 3. By providing the step region 3C, the occurrence of misalignment of the wiring member 5C can be suppressed, and by providing the wiring member 5C, the occurrence of unnecessary wrinkles and the like in the pad 2 can be suppressed. The elastic portion 5C7 is located on the side opposite to the elastic portion 5C6 as viewed from the linear portion 5C4, and when the holder 3 is assembled together with the body 4, the second end portion 5C2 can be brought into contact with the pad side electrode 2F by the biasing force of the elastic portion 5C7.

Embodiments have been described above, but the above disclosure is an example in all respects and no limitation is intended. The technical scope of the present invention is indicated by the scope of the claims, and meanings equivalent to the scope of the claims and all changes within the scope of the claims are intended to be included.

REFERENCE SIGNS LIST

1 Low-frequency treatment device
2 Pad
2A Attachment portion
2B, 2C Treatment portion
2D Conductive layer
2E, 2F Pad side electrode 2G Gel
2H Through hole
2J Insulation region
2S, 3S Front surface
2T, 3T Rear surface
3 Holder
3A Plate-like portion
3B, 4NA, 4NB Protrusion portion
3C Step region
3E, 3F Projection portion
3EA, 3FA Vertical wall portion
3EB, 3FB Top surface portion
3EC, 3FC Receiving portion
3ED, 3FD Insertion hole
3J Engagement portion
3JA, 5C5 Upright portion
3JB Overhang portion
3K Engagement tab
4 Body
4A Case body
4B Operation piece
4B1 Engaged position
4B2 Released position
4C Bias portion
4DA, 4DB Body side electrode
4E Inner peripheral edge
4F, 4P Projection
4G Recess portion
4H Insertion opening
4K Curved portion
4L Flat portion
4MA Insertion piece
4Q Housing portion
4R, 4U Recessed portion
4S Upper surface
4T Lower surface
4TA Projection piece
5A4, 5B4, 5C4 Linear portion
5A, 5B, 5C Wiring member
5A5, 5B5, 5C6 Elastic portion (first elastic portion)
5A6, 5B6, 5C7 Elastic portion (second elastic portion)
5A1, 5B1, 5C1 First end portion
5A2, 5B2, 5C3 Second end portion
5A3, 5B3, 5C3 Conductive portion
8A Symbol
AR Longitudinal direction
DR1, DR2B, DR2A, DR3, DR3B, DR3A, DR4, DR5, DR6A, DR6B, DR7A, DR7B, DR8, DR9 arrow

The invention claimed is:

1. A low-frequency treatment device, comprising:
a pad including a front surface, a rear surface, a through hole that extends from the front surface to the rear surface, and a pad side electrode formed on the rear surface;
a holder including a plate-like portion, the holder being disposed on a rear surface side of the pad such that the plate-like portion opposes the pad side electrode;
a body including an opposite surface and a body side electrode provided on the opposite surface side, the body being disposed such that the opposite surface opposes the front surface of the pad and the body being detachably attached to the holder to sandwich the pad between the opposite surface and the holder; and
a wiring member configured to electrically connect the body side electrode and the pad side electrode, wherein the wiring member includes
a first end portion connected to the body side electrode,
a second end portion connected to the pad side electrode, and
a conductive portion, disposed such that a portion of the conductive portion extends through the through hole, for conducting electricity between the first end portion and the second end portion,
the conductive portion of the wiring member includes a first elastic portion located on a first end portion side, and the first end portion is brought into contact with the body side electrode by a biasing force of the first elastic portion,
the holder further includes an engagement portion that engages with the body, and
in a state where the holder is attached to the body by engaging the engagement portion with the body, the holder is subject to force acting in a direction away from the body by the biasing force of the first elastic portion.

2. The low-frequency treatment device according to claim 1, wherein
the holder includes a projection portion provided to project from the plate-like portion,
in a state where the holder is disposed on the rear surface side of the pad, the projection portion is disposed to extend through the through hole of the pad, and
the portion of the conductive portion of the wiring member disposed to extend through the through hole is held by the projection portion.

3. The low-frequency treatment device according to claim 2, wherein
an insertion opening is formed in the opposite surface of the body,
the body side electrode is provided inside the insertion opening, and
in a state where the body is attached to the holder, the projection portion is inserted into the insertion opening and the first end portion and the body side electrode are brought into contact with one another.

4. The low-frequency treatment device according to claim 1, wherein
the conductive portion of the wiring member includes a second elastic portion located on a second end portion side, and the second end portion is brought into contact with the pad side electrode by biasing force of the second elastic portion.

5. The low-frequency treatment device according to claim 1, wherein
a step region is provided to be recessed in the plate-like portion of the holder, and
the conductive portion of the wiring member includes a portion disposed inside the step region.

6. The low-frequency treatment device according to claim 1, wherein
the rear surface of the pad and the plate-like portion of the holder are joined together via an adhesive portion.

* * * * *